(12) United States Patent
Rafael De Souza et al.

(10) Patent No.: US 7,563,456 B2
(45) Date of Patent: Jul. 21, 2009

(54) PROCESS FOR PREPARATION OF PROGRAMMED LIBERATION COMPOSITION WITH VENLAFAXINE AND THE RESULTING PRODUCT

(76) Inventors: Fernando Rafael De Souza, Chacabuco 96, 2° Piso, 1069 Buenos Aires (AR); Elizabeth Molenda Ferreira Amado, Chacabuco 96, 2° Piso, 1069 Buenos Aires (AR)

( * ) Notice: Subject to any disclaimer, the term of this patent is extended or adjusted under 35 U.S.C. 154(b) by 925 days.

(21) Appl. No.: 10/476,714

(22) PCT Filed: Jan. 3, 2002

(86) PCT No.: PCT/BR02/00001

§ 371 (c)(1),
(2), (4) Date: Nov. 4, 2003

(87) PCT Pub. No.: WO02/102129

PCT Pub. Date: Dec. 27, 2002

(65) Prior Publication Data

US 2004/0131677 A1    Jul. 8, 2004

(30) Foreign Application Priority Data

Jan. 17, 2001    (BR)    .................... 0100334

(51) Int. Cl.
*A61K 9/16*    (2006.01)

(52) U.S. Cl. ........................ 424/490; 424/489; 424/493; 424/494; 424/497

(58) Field of Classification Search ....................... None
See application file for complete search history.

(56) References Cited

U.S. PATENT DOCUMENTS 4,079,125 A * 3/1978 Sipos .......................... 424/480
6,001,848 A * 12/1999 Noble ......................... 514/288

FOREIGN PATENT DOCUMENTS

WO    WO 84/00295    *    2/1984

OTHER PUBLICATIONS

Handbook of Pharmaceutical Excipients, 1988.*

* cited by examiner

*Primary Examiner*—Eric E. Silverman
(74) *Attorney, Agent, or Firm*—Evelyn A. Defilló; Defillo & Associates, Inc

(57) ABSTRACT

Process for the preparation of programmed liberation compositions with venlafaxine and the resulting product, from which the resulting product allows a better absorption of the active principle and a drastic decrease of the adverse effects, due to the preparation methodology. The formulation comprises a first phase, in which the non-active cores are elaborated as spherical micro granules, from sugar and starch. In the second phase, it is added to them the active drug, as impalpable powder, utilizing as binding, a povidone alcoholic solution. In the third phase, it is applied the coating on the micro granules that contain the active drug. At last, in the fourth phase, it is made the encapsulation of the recoated micro granule.

8 Claims, No Drawings

PROCESS FOR PREPARATION OF PROGRAMMED LIBERATION COMPOSITION WITH VENLAFAXINE AND THE RESULTING PRODUCT

CROSS REFERENCE TO RELATED APPLICATION

This application is a national stage of PCT/BR02/00001 filed Jan. 3, 2002 under the International Convention, with priority claimed from Brazilian, Application No. PI 0100334-8, filed Jan. 17, 2001.

FIELD OF INVENTION

The present invention relates to a new formulation of programmed liberation capsules with the active principle Venlafaxine (*) HCl, as well as the resulting product, which presents a larger absorption of active principles and a drastic reduction of adverse effects.

(*)1-[2-(Dimethylamine)-(4-methoxyphenyl)ethyl]ciclohexanol

Various procedures are utilized for the preparation of programmed liberation pharmaceutical products. One procedure, however, includes the slowly soluble matrix tablets, that may lead to the unforeseen suffering of pyloric retention, during the digestive segment, hereby causing the indetermination of the dissolution profile.

The process of the present invention includes the elaboration of prolonged action micro (PAM) granules that contain the active principle. These granules are placed, in large amount, within capsules that upon separating in the gastric lumen, allow the dispersion of the micro granules by all available volume, liberating the active principle in an independent form, thereby acquiring the maintenance of a defined dissolution profile.

The elaboration process further avoids an additional difficulty that presents the Venlafaxine in programmed liberation preparations, such as its high solubility. Once the programmed dissolution is obtained by means of the deposit of a tissue around the micro granules, a sufficient thickness is necessary to regulate in proper form its dissolution speed.

The objective of the present invention is to develop an elaboration methodology that includes prolonged action micro granules containing Venlafaxine, in such a way that allows regulating the thickness of the involved tissue, getting the adequate dissolution profile of the active principle and, consequently, a better absorption of the active principle and decrease of its adverse effects.

BACKGROUND OF THE INVENTION

Regarding the antecedents of the present invention, some previous patents are known in which the methods of elaboration containing Venlafaxine HCl were developed.

In these patents, the cores are elaborated from the mixture of the active drug with microcrystalline cellulose, which is crushed and granulated utilizing hydroxypropilmethylcellulose dispersed in water as binding; such a dispersion may be prepared onsite in previous form. This wet mass is extruded, shaped into spheres, dried and purified (to select granulometries); the micro granules being obtained with the incorporated, and without coating, active drug, with the property of "immediate liberation".

In these same patents, it is also claimed that the elaboration of cores are without the presence of hydroxypropilmethylcellulose, although this is utilized soon after and duly mixed with ethyl cellulose, in the after phase of coating application.

To get the "programmed liberation" properties, the micro granules are covered with a tissue, by the deposition of a mixture of ethyl cellulose and hydroxypropilmethylcellulose. This process is realized in a liquefied bed by aspersion of an ethyl cellulose solution and hydroxypropilmethylcellulose in a solvent consisting of a mixture of methylene chloride and methanol.

SUMMARY OF THE INVENTION

The main objective of the present invention is a new formulation of prolonged liberation capsules containing the Venlafaxine HCl active principle, characterized by presenting a Bioavailability in humans of 2,279 mg.h/mo, and by comprising the following elaboration procedure:

I Elaboration of the non-active core. These cores are elaborating by wetting sugar crystals in a coating boiler with a diluted solution of sugar in water. These wet crystals are powdered with cornstarch, to favor the formation of spheres by the turbulent motion of the crystals within the boiler, and to eliminate the wet excess. These spherical wet cores are dried in a drying stove with forced hot air circulation and then purified to be classified by their granulometry.

II Elaboration of the active core. The inert cores elaborated in the previous phase, are then dried, purified and with adequate granulometry, are placed in a coating boiler of adequate capacity, where they are wetted with a Povidon alcoholic solution (generally an isopropyl alcohol). When the desired stage of humidity is obtained, we begin the powdering of the product within the boiler with Venlafaxine HCl previously grinded until it becomes impalpable powder. When the incorporation of the active principle is finished, the micro granules are passed through a stainless steel sieve with appropriated mesh and then dried in the same moving boiler, with hot air blast, or in a forced hot air drying stove.

III Application of the coating. In the present invention acetone solutions or Ethyl cellulose acetone-alcoholic, which aggregated an adequate plasticizer to lower the vitreous transition temperature, avoids the formation of breakable membranes.

Next two technological possibilities are presented for the obtainment of the membrane that covers the micro granules of quality and thickness; enough to attain the desired programmed dissolution profile.

With coating boiler. In the same boiler in which the active micro granules are elaborated, they are powdered with the same Ethyl cellulose solution. The evaporation of the solvent leaves the micro granule coated with a fine coat of plasticized ethyl cellulose. The thickness of the coat is regulated through the quantity of applied solution. The product is left to dry by rotation in a boiler with hot air blast, or placed in a stove with forced hot air. The deposition of crescent quantities of the coating tissue is not realized, until it obtains the desired in-vitro dissolution.

Liquefied bed with Wurster. In this case, a previous preparation of "naked" micro granules is required, along with those obtained in the first phase. Due to the energetic motion within the Wurster, the micro granules are hardened in the coating boiler, first a PVP pre-coat, and then ethyl cellulose. Finally, it is ended with the powdered coating, on the micro granules placed in the liquefied bed; the same solution that is applied in the coating boiler.

The differences between both steps are as follows:

a) In the Wurster, the application of the coating is more effective, obtaining equal tissue thickness, with less quantities of applied solution.

b) The processes are more productive in the Wurster, than in traditional coating boilers. Nonetheless, the product is more accessible because an eventual difficulty in the process may be detected and corrected faster.

c) In the conventional coating boilers, the product is not subjected to mechanical stress that the liquefied bed suffers, obtaining a smaller production of powder that is not desired.

Comparing the current method with the previous ones, we describe below the components of the different procedures:

| Previous | Current |
|---|---|
| Venlafaxine HCl | Venlafaxine HCl |
| Microcrystalline Cellulose | Non active cores (sugar, starch) |
| Hydroxypropyltmethylcellulose | PVP |
|  | Talc |
| Ethyl cellulose | Ethyl cellulose |
|  | Plasticizer |

As to the difference of the elaboration method: 2

| Previous | Current |
|---|---|
| Elaboration of the (active) core Mixture of drug + microcrystalline cellulose + hydroxypropylmethylcellulose/ wetting/kneaded/extrusion/ shaping into sphere | Elaboration of the (non active) core: Application of starch on sugar crystals, using sugar in water solution as binder |
|  | Elaboration of the (active) core: Application of grinded drug on non-active cores, using PVP alcoholic solution as binder. |
| Coating: Ethyl cellulose + hydroxypropylmethylcellulose/ Deposited from a solvent constituted by methanol-methylene chloride. | Coating: Ethyl cellulose + Plasticizer/ Deposited from a solvent constituted by acetone or acetone + isopropylalcohol. |
| Employed machine incoating: Only liquefied bed | Employed machine in coating: liquefied bed or coating boiler. |

As it regards to an extremely soluble drug, the dissolution profile of the same is exclusively regulated by the quality and thickness of the coating tissue. Thus, both technologies, the previous and the current one, may lead to similar products from the point of view of its bioavailability. However, it was possible to demonstrate, in a comparative study made in humans, that the process of the present invention led to the obtainment of a superior product, because of its better absorption, than that obtained by previous methods.

DETAILED DESCRIPTION OF THE INVENTION

As referred to earlier, the process of the present invention is more versatile, due to the fact that not every active principle may be elaborated by kneading, extruding and shaping it into the sphere method. Particularly, if the required concentration is so high that it presents a very narrow margin for the aggregate, the kneading, extrusion and shaping it into the sphere could not be possible.

Going now to a more detailed description of the present invention; the following examples show how it can be put into practice:

1. Batch: PE9942—First Phase 400 grams of active drug were kneaded and applied, in a coating boiler, on 200 grains of sugar and starch cores. As binder, it utilized a PVP solution at 5% in isopropyl alcohol. During the process, the granulometry of the product was kept constant by the depuration and classification by size, made periodically. Once the entire active drug was applied, the coating of the product with 100 grams talk was made, using additional PVP solution. The total PVP solution utilized was 800 ml. The product was dried overnight at 45° C., and made the corresponding controls, that included:

Weight: 480 grams

Title: 450.7 mg/g

Dissolution: 103%

Capability of capsule: N.degree. 0=461.6 mg/capsule

N.degree. 1=333.2 mg/capsule

2. Batch: PE 9942—Second Phase

From the batch obtained in example 1, 300 grams of micro granules were separated and placed in an experimental equipment of a liquefied bed. In this equipment, crescent quantities of 10% plasticized ethylcellulose were applied, calculated on Mygliol contained solids. The ethyl cellulose was at 3% in acetone and the operative conditions of the equipment were those traditional for this type of coating. During the process of coating, it was noted that it was necessary to periodically powder the product with talk, in order to diminish the static load, and the mechanical conditions occasioned to rupture some of the micro granules. With a total applied volume of about 2.920 liters/kg of micro granules, the value and the dissolution profile is as follows:

Value: 409.54 mg/g

Dissolution

After 1 hour: 20.0%

After 4 hours: 58.0%

After 8 hours: 75.7%

After 24 hours: 96.7%

3. Batch: PE10326—First Phase 29.500 kg of active drug were kneading and incorporated, in a coating boiler of adequate size, on 14.750 kg of sugar and starch cores. With binding solution, approximately 30 liters of PVP solution at 5% in isopropyl alcohol was used. The sizes were equalized, where possible, and the obtained product was coated with 8.850 kg of talk, utilizing 5 additional liters of PVP solution. The product was dried in a stove at 45° C., and once the balance (yield) of drug was analyzed, a pre-cover of coating in the same boiler was applied: 4 liters of PVP at 10% in isopropyl alcohol were incorporated, followed by 24 liters of plasticized ethyl cellulose at 3% in acetone. This product was approved by the Quality Control in order to continue the process of obtainment of the programmed dissolution, as discussed in the following example 4.

4. Batch: PE 10326 and 10328—Second Phase

Half of the parcel obtained in example 3 was placed in a liquefied bed with Wurster and the same ethyl cellulose solution was applied at a rate of 1.5 liters/kg of micro granules. This procedure was repeated with the second half. The mixture of both fractions was encapsulated by adding in capsules No. 1 with a dosage of 75 mg Venlafaxine Base, and in capsules No. 0 with a dosage of 150 mg Venlafaxine Base.

The products were obtained with the following features:

| 10326<br>Each capsule contains 74.8 mg<br>Venlafaxine Base | 10328<br>Each capsule contains 149, mg<br>Venlafaxine Base |
|---|---|
| Dissolution: | |
| After 1 hour: | 5.4% |
| After 4 hours: | 46.5% |
| After 8 hours: | 74.8% |
| After 24 hours: | 100.0% |

5. Batch: 10329 and 10330—First Phase.

3.500 kg of Venlafaxine HCl were kneaded and applied in an adequately sized boiler, on 1.750 kg of sugar and starch core. The binding solution was PVP at 5% in isopropyl alcohol, and about 7:000 liters were used. Once the application of the active principle was complete, the obtained product was coated with 1.050 kg of talk. The analytical profile of the product is as follows:

Weight: 6.300 kg

Value: 510.5 mg/g

Balance of the drug: 3.216 kg (yield: 91.9%)

Dissolution: 105% in 1 hour

6. Batch 10329 and 10330—Second Phase.

The product obtained in example 5 was coated in the same coating boiler in which it was elaborated. The solution employed for the coating consisted of ethyl cellulose in acetone and isopropyl alcohol. The solution was applied on the micro granules until a satisfactory profile in dissolution was obtained. After that the micro granules were encapsulated in capsules No. 1 for the 75 mg dosage and in capsules No. 0 for the 150 mg dosage. The obtained capsules contained 73.8 mg and 143.8 mg of Venlafaxine Base, respectively, and a dissolution as described below:

| Time | Dissolution |
|---|---|
| After 1 hour | 30.5% |
| After 4 hours | 58.8% |
| After 8 hours | 70.2% |
| After 24 hours | 87.1% |

Bioavailability in Humans.

A study was conducted entitled: "Comparative study of plasmatic concentrations of Venlafaxine after administering a programmed liberation formulation (1.times.50 mg), one of sustained liberation (1.times.50 mg) and one immediate liberation reference (2.times.75 mg) in healthy volunteers."

Such study was presented at INAME and its results, measured according to the pharmacokinetic AUC tot parameter, concluded that the absorption of the product in humans, whose formulation is claimed, is similar to that observed with 2 taken from the reference product mg), while it is 28% superior, compared to previous prolonged action formulations [2.279 ng.h/ml versus 1.751 ng.h/ml].

It is also proven that the adverse effects of the formulation being claimed, are reduced by 50% compared to those caused by the reference formulation, due to the plasmatic concentration peak being reduced as it is a programmed liberation formulation.

The invention claimed is:

1. A Process for producing a controlled release encapsulated composition having venlafaxine as active ingredient, the process comprising the steps of:
    A) preparing a non-active core by:
        wetting sugar crystals in a coating boiler with a diluted solution of sugar in water;
        powdering the crystal with corn starch to obtain spherical micro granules;
        drying the spherical micro granulates;
        classifying the dried spherical micro granulates by granulometry;
    B) preparing an active core by:
        placing the dried spherical micro granulates of the previous step in a coating boiler;
        wetting the dried spherical micro granulates in the coating boiler with PVP dissolved in isopropyl alcohol;
        powdering the wet spherical micro granulates with powdered venlafaxine HCl;
        wetting the granulated powder with venlafaxine HCL with additional PVP dissolved in isopropyl alcohol and powdering with talc;
        drying the granulates;
    C) applying a coating over the active core, wherein the coating contains at least one of ethyl cellulose, Shellac, or Cellulose Esters; and
    D) encapsulating the coated active core.

2. The process according to claim 1 wherein the active ingredient is Venlafaxine HCl in an amount between 10% and 80% by weight of the final product.

3. The process according to claim 1 wherein the coating of the micro granules with the active drug is performed in a coating boiler.

4. The process according to claim 1 wherein the coating of the micro granules with the active drug is performed in a fluidized bed granulation coater using the Wurster method.

5. The process according to claim 1 wherein the coating over the active core comprises ethyl cellulose and further comprises includes a plasticizer in an amount between 0.01% and 5% by weight of the final product to avoid the formation of breakable membranes.

6. The process according to claim 5 wherein the plasticizer is selected from the group consisting of coconut oil, Castor Oil, Honeybee Waxes, Phthalic Esters, and mixtures thereof.

7. An encapsulated composition having venlafaxine as the active ingredient comprising:
    A) a non-active core produced by:
        wetting sugar crystals in a coating boiler with a diluted solution of sugar in water;
        powdering the crystal with corn starch to obtain spherical micro granules;
        drying the spherical micro granulates;
        classifying the dried spherical micro granulates by granulometry;
    B) an active core produced by:
        placing the dried spherical micro granulates of the previous step in a coating boiler;
        wetting the dried spherical micro granulates in the coating boiler with PVP dissolved in isopropyl alcohol;
        powdering the wet spherical micro granulates with powdered venlafaxine HCl;
        wetting the granulated powder with venlafaxine HCL with additional PVP dissolved in isopropyl alcohol and powdering with talc;
        drying the granulates;

C) a coating over the active core, wherein the coating contains ethyl cellulose; and D) encapsulating the coated active core.

8. An encapsulated composition having venlafaxine as the active ingredient consisting of:

a non-active core produced by:
- wetting sugar crystals in a coating boiler with a diluted solution of sugar in water;
- powdering the crystal with corn starch to obtain spherical micro granules;
- drying the spherical micro granules;
- classifying the dried spherical micro granules by granulometry;

B) an active core produced by:
- placing the dried spherical micro granules of the previous step in a coating boiler;
- wetting the dried spherical micro granulates in the coating boiler with PVP dissolved in isopropyl alcohol;
- powdering the wet spherical micro granulates with powdered venlafaxine HCl;
- wetting the granulated powder with venlafaxine HCL with additional PVP dissolved in isopropyl alcohol and powdering with talc;
- drying the granulates;

C) a coating over the active core, wherein the coating contains ethyl cellulose; and D) wherein the coated micro granulated is encapsulated.

* * * * *